United States Patent
Bajraszewski et al.

(10) Patent No.: US 9,310,187 B2
(45) Date of Patent: Apr. 12, 2016

(54) IMAGE CAPTURING APPARATUS, IMAGE CAPTURING METHOD, AND STORAGE MEDIUM

(71) Applicant: CANON KABUSHIKI KAISHA, Tokyo (JP)

(72) Inventors: Tomasz Bajraszewski, Głogowo (PL); Hirofumi Yoshida, Yokohama (JP); Marek Różański, Toruń (PL); Maciej Szkulmowski, Toruń (PL)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/797,361

(22) Filed: Jul. 13, 2015

(65) Prior Publication Data

US 2015/0313461 A1 Nov. 5, 2015

Related U.S. Application Data

(63) Continuation of application No. 13/959,975, filed on Aug. 6, 2013, now Pat. No. 9,109,870.

(30) Foreign Application Priority Data

Aug. 30, 2012 (JP) ................. 2012-190642

(51) Int. Cl.
*G01B 9/02* (2006.01)
*G02B 27/14* (2006.01)
*A61B 3/14* (2006.01)
*A61B 3/10* (2006.01)
*A61B 3/12* (2006.01)

(52) U.S. Cl.
CPC ............ *G01B 9/02091* (2013.01); *A61B 3/102* (2013.01); *A61B 3/14* (2013.01); *G01B 9/02058* (2013.01); *G02B 27/141* (2013.01); *A61B 3/1233* (2013.01)

(58) Field of Classification Search
CPC ........... G01B 9/02084; G01B 9/20803; G01B 9/02058; G01B 9/02091; A61B 3/1233
See application file for complete search history.

(56) References Cited

U.S. PATENT DOCUMENTS

| 5,513,273 | A | * | 4/1996 | Ito ................................. 382/132 |
| 6,191,862 | B1 | | 2/2001 | Swanson et al. |
| 6,501,551 | B1 | | 12/2002 | Tearney et al. |

(Continued)

FOREIGN PATENT DOCUMENTS

| JP | 2007-057572 A | 3/2007 |
| JP | 2010-012111 A | 1/2010 |

*Primary Examiner* — Michael A Lyons
*Assistant Examiner* — Maurice Smith
(74) *Attorney, Agent, or Firm* — Fitzpatrick, Cella, Harper & Scinto

(57) ABSTRACT

An image capturing apparatus includes a dividing unit configured to divide light from a light source into reference light and measurement light; a first dichroic mirror arranged in a measurement optical path for guiding the measurement light to an object to be examined; a second dichroic mirror arranged in a reference optical path for guiding the reference light to a reference object; and a light receiving unit configured to receive interference light between the measurement light passing through the first dichroic mirror and the reference light passing through the second dichroic mirror.

12 Claims, 6 Drawing Sheets

(56) References Cited

U.S. PATENT DOCUMENTS

| | | |
|---|---|---|
| 6,611,338 B1 | 8/2003 | Knuttel et al. |
| 7,510,282 B2 | 3/2009 | Ueno et al. |
| 7,725,169 B2 | 5/2010 | Boppart et al. |
| 7,880,895 B2 | 2/2011 | Yamada et al. |
| 8,294,901 B2 | 10/2012 | Yoshida et al. |
| 8,308,297 B2 | 11/2012 | Hirose et al. |
| 8,425,036 B2 | 4/2013 | Yoshida et al. |
| 8,502,978 B2 | 8/2013 | Hidaka |
| 8,553,219 B2 | 10/2013 | Patil et al. |
| 2005/0140982 A1 | 6/2005 | Chen et al. |
| 2007/0042275 A1 | 2/2007 | Kamo |
| 2010/0014089 A1 | 1/2010 | Yamada et al. |
| 2010/0182610 A1 | 7/2010 | Utsunomiya |
| 2011/0157552 A1* | 6/2011 | Bublitz et al. ............... 351/209 |
| 2012/0250029 A1 | 10/2012 | Yoshida |
| 2013/0021575 A1 | 1/2013 | Yoshida et al. |
| 2013/0107269 A1* | 5/2013 | Shioda ........................ 356/451 |
| 2013/0194541 A1 | 8/2013 | Aoki et al. |
| 2013/0194542 A1 | 8/2013 | Aoki et al. |
| 2013/0194581 A1 | 8/2013 | Yoshida |

\* cited by examiner

IMAGE CAPTURING APPARATUS, IMAGE CAPTURING METHOD, AND STORAGE MEDIUM

This application is a continuation of U.S application Ser. No. 13/959,975 filed Aug. 6, 2013.

BACKGROUND OF THE INVENTION

1. Field of the Invention

The present invention relates to an image capturing apparatus, an image capturing method, and a storage medium.

2. Description of the Related Art

Currently, various ophthalmic apparatuses using optical apparatuses are known. For example, various apparatuses such as an anterior ocular segment image capturing apparatus, fundus camera, and SLO (Scanning Laser Ophthalmoscope) are used as apparatuses for the observation of the eyes. Among these apparatuses, an optical coherence tomography apparatus based on OCT (Optical Coherence Tomography) using multiwavelength light wave coherence can obtain a tomographic image of a sample at high resolution. The optical coherence tomography apparatus is therefore becoming indispensable to outpatient clinics specialized in retinas as an ophthalmic apparatus.

An optical coherence tomography apparatus (to be referred to as an "OCT apparatus" hereinafter) irradiates an object to be examined with measurement light which is low-coherent light, and can perform high-sensitivity measurement of backscattered light from the object by using a coherent system or coherent optical system. Low-coherent light has the property of being able to obtain a high-resolution tomographic image by increasing the wavelength width. In addition, the OCT apparatus can obtain a high-resolution tomographic image by scanning measurement light on an object to be examined. Therefore, the OCT apparatus can obtain a tomographic image of the retina at the fundus of an eye to be examined as an object to be examined, and hence has been widely used for ophthalmic care and the like for the retina.

On the other hand, the OCT apparatus is generally equipped with optical systems for fundus observation, anterior eye observation, and the like to implement alignment adjustment between the apparatus and an eye to be examined. In order to use the OCT apparatus together with these optical systems, the apparatus is configured to use light sources of different wavelengths for the respective optical systems and perform optical path separation depending on the wavelengths by performing wavelength separation using an optical path branching unit such as a dichroic mirror. The tomographic image acquired by the OCT apparatus will undergo the correction processing of restoring the phase shifted by the dispersion of light for each wavelength in consideration of the dispersion of light at the measurement optical unit and the reference optical unit. For example, according to Japanese Patent Laid-Open No. 2010-12111, dispersion correction is performed by calculating a phase shift amount based on a fundus tomographic image.

Increasing the accuracy of wavelength separation by the dichroic mirror which is the optical path branching unit described above will increase the number of films of the dichroic mirror. This makes the dichroic mirror have phase characteristics showing arbitrary curves (different phase characteristics) in accordance with the wavelengths of light. The different phase characteristics include a phase characteristic which can be corrected in consideration of dispersion and an irregular phase characteristic which cannot be corrected even in consideration of dispersion. With regard to irregular phase characteristics, it is impossible to correct an OCT image by the above correction processing with consideration to dispersion. This can cause the problem that the OCT image (the tomographic image of the object to be examined) blurs in the optical axis direction. It is preferable to acquire a tomographic image of the object with high accuracy even if the phase characteristics of interference light include a phase characteristic which can be corrected in consideration of dispersion and an irregular phase characteristic which cannot be corrected even in consideration of dispersion.

In consideration of the related art, the present invention provides an imaging technique which can acquire a tomographic image of an object to be examined with high accuracy even if the phase characteristics of interference light include a phase characteristic which can be corrected in consideration of dispersion and an irregular phase characteristic which cannot be corrected even in consideration of dispersion.

SUMMARY OF THE INVENTION

The present invention in its first aspect provides an image capturing apparatus comprising: a dividing unit configured to divide light from a light source into reference light and measurement light; a first dichroic mirror arranged in a measurement optical path for guiding the measurement light to an object to be examined; a second dichroic mirror arranged in a reference optical path for guiding the reference light to a reference object; and a light receiving unit configured to receive interference light between the measurement light passing through the first dichroic mirror and the reference light passing through the second dichroic mirror.

The present invention in its second aspect provides an image capturing method for an image capturing apparatus including a dividing unit configured to divide light from a light source into reference light and measurement light, a first dichroic mirror arranged in a measurement optical path for guiding the measurement light to an object to be examined, and a second dichroic mirror arranged in a reference optical path for guiding the reference light to a reference object, the method comprising a step of receiving interference light between the measurement light passing through the first dichroic mirror and the reference light passing through the second dichroic mirror.

According to the present invention, it is possible to acquire a tomographic image of an object to be examined with high accuracy even if the phase characteristics of interference light include a phase characteristic which can be corrected in consideration of dispersion and an irregular phase characteristic which cannot be corrected even in consideration of dispersion.

Further features of the present invention will become apparent from the following description of exemplary embodiments and with reference to the drawings.

DESCRIPTION OF THE EMBODIMENTS

Embodiments of the present invention will be exemplarily described in detail below with reference to the accompanying drawings. The constituent elements described in these embodiments are merely examples, and the technical range of the present invention is defined by the appended claims, but is not limited to each embodiment described below.

First Embodiment

Figure 1:
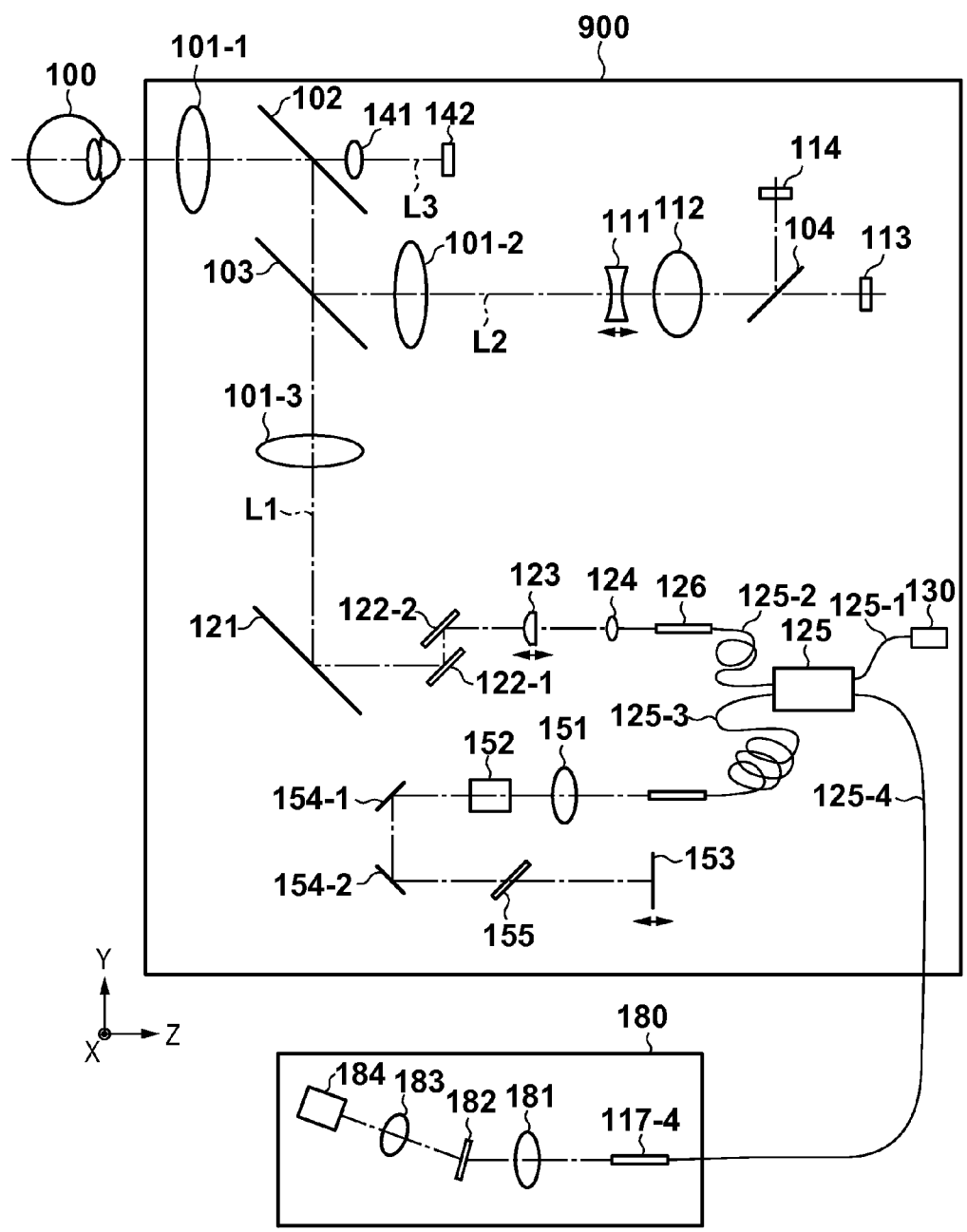
FIG. 1 is a view showing the schematic arrangement of an optical coherence tomography apparatus according to the first embodiment.

FIG. 1 is a view showing the schematic arrangement of an image capturing apparatus (optical coherence tomography apparatus: OCT apparatus). An optical head 900 acquires an image, which could be a two-dimensional image or three-dimensional image, of the object 100, 202 to be examined. For example, the anterior ocular segment or fundus 202 of the eye 100 might be examined.

An objective lens 101-1 is placed in the optical head 900 at a position facing the object 100, for example the eye, to be examined. A first dichroic mirror 102 as a component of an optical path branching unit is placed within the optical path of the objective lens 101-1. A second dichroic mirror 103 as a component of the optical path branching unit is placed within the optical path of light reflected by the first dichroic mirror 102.

The first dichroic mirror 102 and the second dichroic mirror 103 function as optical path branching units which reflect or transmit light in accordance with the wavelength band of the light to guide the light to the object 100, 202 to be examined and guide the return light from the object to an optical path in accordance with the wavelength of the return light. The optical path along which light is reflected by the first dichroic mirror 102 and transmitted through the second dichroic mirror 103 is defined as a measurement optical path L1 of an OCT optical system. In addition, the optical path of light reflected first by the first dichroic mirror 102 and then reflected by the second dichroic mirror 103 is defined as a fundus 202 observation optical path/fixation lamp optical path L2. The optical path of light transmitted through the first dichroic mirror 102 is defined as an anterior eye observation optical path L3.

A lens 141 and an infrared first imaging unit CCD 142 for observing the anterior ocular segment as a first region are arranged on the anterior eye observation optical path L3. The infrared first imaging unit CCD 142 has sensitivity at the wavelength of anterior eye observation illumination light (not shown), more specifically, near 970 nm as a first wavelength. The light emerging from the anterior eye observation illumination light (not shown) and reflected by an eye 100 to be examined is transmitted through the first dichroic mirror 102 and reaches the infrared first imaging unit CCD 142. Note that numerical values such as the values of wavelengths are exemplary and not limited to the above values. The same applies to the following numerical values such as the values of wavelengths.

A third dichroic mirror 104 is placed within the fundus observation optical path/fixation lamp optical path L2. The third dichroic mirror 104 branches the optical path in accordance with the wavelength band of light. The light reflected by the third dichroic mirror 104 branches to a second imaging unit CCD 114 for the observation of the fundus 202 as a second region. The light emerging from a fixation lamp 113 is transmitted through the third dichroic mirror 104. The fixation lamp 113 emits visible light to make the object 100, 202 to be examined hold visual fixation.

Lenses 101-2, 111, and 112 are arranged on the fundus observation optical path/fixation lamp optical path L2. Of these lenses, one lens 111 is a lens for focus adjustment, which is moved by a motor (not shown) on an optical path for focus adjustment for fixation lamp and fundus observation. The second imaging unit CCD 114 acquires an image for fundus observation. The second imaging unit CCD 114 has sensitivity at the wavelength of fundus observation illumination light, more specifically, near 780 nm as a second wavelength. This embodiment is configured to enable the second imaging unit CCD 114 to acquire an observation image of the fundus 202. However, the embodiment may be configured differently. For example, the embodiment may be configured to scan light from a laser on the fundus 202 by using a scanner, receive the reflected light from the scanned fundus via a light-receiving element, and form an observation image of the fundus 202.

The measurement optical path L1 is a component of the OCT optical system and an optical path for irradiating the object 100, 202, for example the fundus 202 of the eye 100, to be examined with light and guiding the light returned from the object to acquire a tomographic image of the object. A lens 101-3, a mirror 121, and a measurement light scanning unit, including an X scanner 122-1 and a Y scanner 122-2, for scanning light on the object 100, 202 to be examined are arranged on the measurement optical path L1.

A fiber end 126 is a measurement light source for enabling measurement light to enter the measurement optical path L1. The fiber end 126 is placed at a position optically conjugate to the object 100, 202 to be examined. Lenses 123 and 124 are arranged between the Y scanner 122-2 and the fiber end 126. Of these lenses, one lens 123 is a lens for focus adjustment and is moved within the optical path by a motor (not shown) for focus adjustment for the measurement of the object. Focus adjustment is performed to form light emerging from the fiber end 126 into an image on the object 100, 202 to be examined. Although the optical path between the X scanner 122-1 and the Y scanner 122-2 of the measurement light scanning unit looks as if it were formed within the drawing surface, the optical path is actually formed in a direction perpendicular to the drawing surface.

The arrangement of optical paths from a measurement light source 130 as a reference optical system and spectroscope will be described next. An optical element having a phase characteristic relative to the phase characteristic of a dichroic mirror as a component of an optical path branching unit is placed within a reference optical path which guides reference light. An additional optical element having the same phase characteristic as that corresponding to the wavelength of the measurement light source of an optical element, such as a dichroic mirror, as a component of the optical path branching unit is placed within the reference optical path as a phase characteristic corresponding to the wavelength of the measurement light source. Note that the above phase characteristics are not limited to identical characteristics. The phase characteristics differ from each other due to errors in the manufacturing process of each optical element. In consideration of such errors, optical elements as components of the reference light and optical path branching unit may be those having almost identical phase characteristics.

The measurement light source 130, an optical coupler 125, single-mode optical fibers 125-1 to 125-4 connected to the optical coupler 125 to be integrated, a lens 151, a dispersion compensation glass 152, a reference mirror 153, and a spectroscope 180 constitute a Michelson interferometer system. The light emitted from the measurement light source 130 passes through the optical fiber 125-1 and is divided into measurement light on the optical fiber 125-2 side and reference light on the optical fiber 125-3 side through the optical coupler 125. The measurement light irradiates the object 100, 202, for example the eye, to be examined as an observation target through the measurement optical path L1 of the OCT optical system described above. That is, after the measurement light is reflected by the mirror 121, the light is transmitted through the second dichroic mirror 103 and reflected by the first dichroic mirror 102 to reach the object 100, 202. The return light, including reflected light and scattered light, from the object 100, 202, for example the retina in the case of the eye, is examined and reaches the optical coupler 125 through the measurement optical path L1.

On the other hand, the optical fiber 125-3, the lens 151, the dispersion compensation glass 152, a mirror 154-1, a mirror 154-2, a glass plate 155, and the reference mirror 153 constitute a reference optical path as an optical path through which reference light passes. Note that the mirror 154-1 and the mirror 154-2 may be plates having mirror-polished surfaces to reflect light, as optical elements. Reference light is reflected by the mirror 154-1 and the mirror 154-2 through the optical fiber 125-3, the lens 151, and the dispersion compensation glass 152 which is inserted to match the dispersion of measurement light with that of reference light. The reflected light then reaches the reference mirror 153 through the glass plate 155. The reference light which has reached the reference mirror 153 is reflected by the reference mirror 153 in the original direction to return along the same reference optical path, and reaches the optical coupler 125. Note that the above arrangement may exclude the glass plate 155.

This arrangement uses, as one of the mirror 154-1 and the mirror 154-2, a mirror having the same phase characteristic relative to the wavelength of incident light as that of the first dichroic mirror 102. For example, the arrangement uses, as one of the mirror 154-1 and the mirror 154-2, a mirror identical to the first dichroic mirror 102. In addition, the mirror 154-1 or the mirror 154-2 is configured such that the incident angle of light on it becomes equal to that (for example, about 45°) on the first dichroic mirror 102. Note that the incident angle of light on the mirror 154-1 or the mirror 154-2 need not always be perfectly equal to that on the first dichroic mirror 102. That is, the above incident angles of light may be almost equal to each other. This means the term "equal" is used within this specification as a concept including both a case in which the incident angles are perfectly equal and a case in which they are almost equal. A mirror having the same phase characteristic as that of the first dichroic mirror 102 is placed within the reference optical path such that the incident angles become equal to each other. This cancels out a phase characteristic relative to the wavelength of incident light between the measurement optical path L1 and the reference optical path. This makes it possible to cancel out or to reduce the influence of different phase characteristics in accordance with the wavelength of light of the first dichroic mirror, including a phase characteristic which can be corrected in consideration of dispersion and an irregular phase characteristic which cannot be corrected even in consideration of dispersion. For the same purpose, the second dichroic mirror 103 and the glass plate 155 have the same phase characteristics. For example, the glass plate 155 uses the same mirror as the second dichroic mirror 103. In addition, the second dichroic mirror 103 and the glass plate 155 are arranged so as to set the same incident angle (for example, almost 45°).

In this embodiment, the mirror 154-1 or the mirror 154-2 has a phase characteristic corresponding to the phase characteristic of the first dichroic mirror 102, and the glass plate 155 has a phase characteristic corresponding to the phase characteristic of the second dichroic mirror 103. However, the embodiment is not limited to this. An optical element placed within the reference optical path need not have a phase characteristic corresponding to that of an optical element of the optical path branching unit as long as it is possible to form a tomographic image which does not blur in the optical axis direction due to the correction processing of restoring a phase shifted by light dispersion. If, for example, a tomographic image of the object 100, 202 to be examined can be acquired by the correction processing of restoring a phase shifted by light dispersion for each wavelength, the mirror 154-1 or the mirror 154-2 need not have a phase characteristic corresponding to that of the first dichroic mirror 102. Alternatively, the glass plate 155 need not have a phase characteristic corresponding to that of the second dichroic mirror 103. The case in which it is possible to acquire a tomographic image of the object 100, 202 to be examined by the correction processing of restoring a phase shifted by light dispersion for each wavelength includes, for example, the case in which it is possible to perform correction processing in consideration of dispersion concerning one of the first dichroic mirror 102 and the second dichroic mirror 103. If, for example, the number of films of one dichroic mirror is small and phase characteristics include no or only a limited number of irregular phase characteristics which cannot be corrected even in consideration of dispersion, correction processing as numerical processing can reduce the influences of phase characteristics. In this case, one dichroic mirror 102, 103, 104, 155, 182 need not have a phase characteristic corresponding to that of the mirror 154-1, 154-2 or glass plate 155 on the reference optical path. In addition, if correction processing can reduce the influence of phase characteristics concerning one dichroic mirror 102, 103, 104, 155, 182, one dichroic mirror 102, 103, 104, 155, 182 need not have a phase characteristic corresponding to that of the mirror 154-1, 154-2 or glass plate 155 on the reference optical path.

The optical coupler 125 combines return light from the object 100, 202 to be examined with reference light propagating through the reference optical path into interference light. In this case, when the optical path length of the measurement optical path becomes almost equal to that of the reference optical path, measurement light and reference light cause interference. The reference mirror 153 is held by a motor and a driving mechanism (neither are shown) so as to be adjustable in the optical axis direction. This makes it possible to match the optical path length of reference light with that of measurement light which changes depending on the object 100, 202, for example the eye, to be examined. The interference light is guided to the spectroscope 180 through the optical fiber 125-4.

The spectroscope 180 is constituted by lenses 181 and 183, a diffraction grating 182, and a line sensor 184. The interference light emerging from an optical fiber 117-4 is almost collimated through the lens 181 and then spectroscoped by the diffraction grating 182. The lens 183 forms the resultant light into an image on the line sensor 184.

The measurement light source 130 will be described next. As the measurement light source 130, it is possible to use, for example, an SLD (Super Luminescent Diode), which is a typical low-coherent light source. The SLD 130 emits light having a center wavelength of 855 nm and a wavelength bandwidth of about 100 nm. In this case, a bandwidth influences the resolution of an obtained tomographic image in the optical axis direction, and hence is an important parameter. The type of light source to be used is not limited to the SLD 130. It is possible to use an ASE (Amplified Spontaneous Emission) light source or the like as long as it can emit low-coherent light. In consideration of measurement of the object 100,202 to be examined, for example, the eye, the wavelength of near-infrared light is suitable as the center wavelength of light to be used. In addition, the center wavelength influences the resolution of an obtained tomographic image in the lateral direction, and hence is preferably as short as possible. For the above two reasons, the center wavelength is set to 855 nm.

This embodiment makes use of a Michelson interferometer as an interferometer. However, the scope of the present invention is not limited to this configuration. For example, a Mach-Zehnder interferometer may be used as a possible alternative. It is preferable to use a Mach-Zehnder interferometer if the light amount between measurement light and reference light differs greatly, whereas it is preferable to use a Michelson interferometer instead if the light amount difference between measurement light and reference light is small.

A method of capturing a tomographic image of the object 100, 202 to be examined by using the OCT apparatus will be described now in more details. The OCT apparatus can acquire a tomographic image of a desired region of the object 100, 202, for example the fundus 202 of the eye 100, to be examined by controlling the measurement light scanning unit, including the X scanner 122-1 and the Y scanner 122-2.

Figure 2:
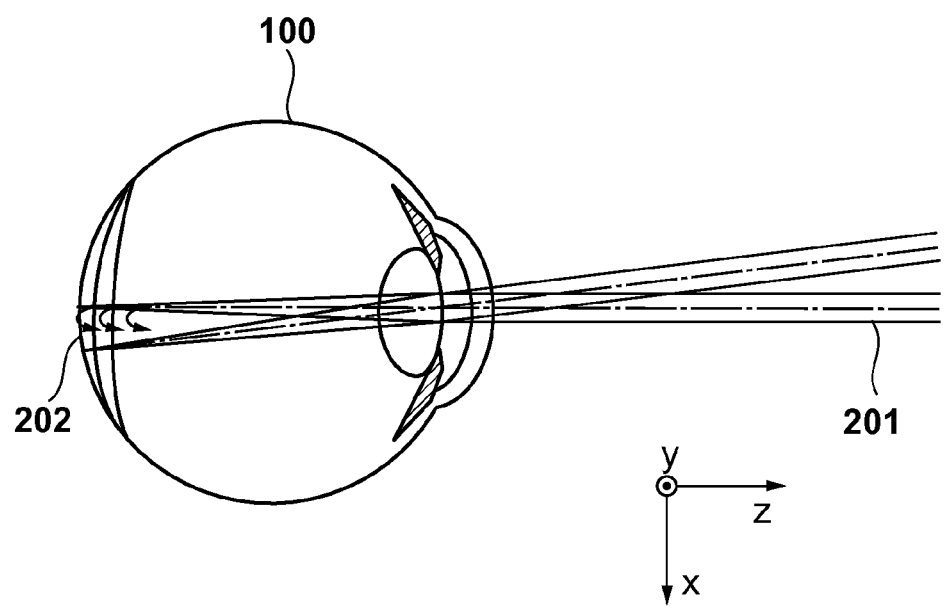
FIG. 2 is a view showing an example of scanning measurement light on an object to be examined.

FIG. 2 shows how the OCT apparatus irradiates the object 100, 202 to be examined with measurement light 201 and scans the measurement light 201 on the fundus 202 of the object 100, 202 in the x direction. The line sensor 184 in FIG. 1 receives return light corresponding to a predetermined imaging count from the imaging range of the fundus 202 in the x direction. The apparatus performs FFT (Fast Fourier Transform) for a luminance distribution on the line sensor 184 which is obtained at a given position in the x direction, converts the linear luminance distribution obtained by FFT into density or color information to be displayed on a monitor. This information will be referred to as an A scan image. A two-dimensional image obtained by arranging a plurality of A scan images will be referred to as a B scan image. Upon capturing a plurality of A scan images to construct one B scan image, the apparatus performs scanning in the x direction again by moving the scan position in the y direction, thereby obtaining a plurality of B scan images. A display unit 300 displays a plurality of B scan images or a three-dimensional tomographic image constructed from the plurality of B scan images to allow the examiner to use the images for the diagnosis of the eye 100 or the fundus 202 to be examined.

Figure 3:
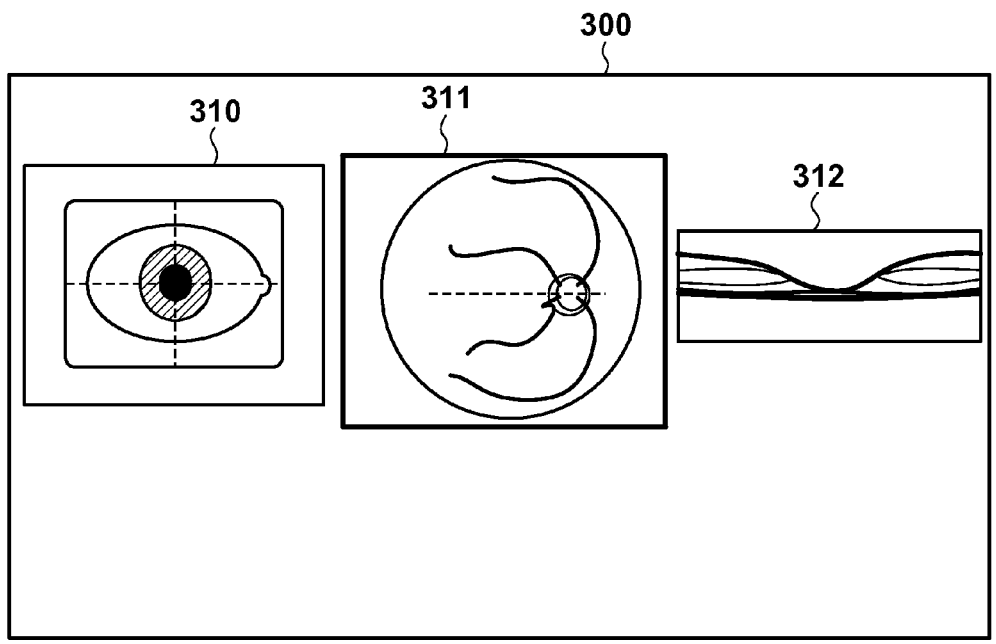
FIG. 3 is a view exemplifying the display on a display unit.

FIG. 3 is a view exemplifying the display on the display unit 300. The display unit 300 displays a two-dimensional anterior eye image 310, a fundus image 311, and a tomographic image 312 side by side. The anterior eye image 310 is an image processed and displayed based on an output from the infrared CCD 142. The fundus image 311 is an image processed and displayed based on an output from the CCD 114. The tomographic image 312 is constructed by the above processing based on an output from the line sensor 184.

According to this embodiment, it is possible to acquire a tomographic image of the object 100, 202 to be examined with high accuracy even if the phase characteristics of the optical path branching unit of the measurement optical unit including a phase characteristic which can be corrected in consideration of dispersion and an irregular phase characteristic which cannot be corrected even in consideration of dispersion.

Second Embodiment

The first embodiment has exemplified the arrangement as an arrangement for correcting the phase characteristics of the optical path branching unit, in which an optical element having a phase characteristic corresponding to that of a dichroic mirror as a component of the optical path branching unit is placed within the reference optical path which guides reference light. The second embodiment discloses an arrangement configured to remove the influences of phase characteristics on the overall measurement optical unit, such as optical path branching units, lenses, mirrors, optical fiber, and the like on a measurement optical path L1, for receiving the interference light between return light and reference light by numerical arithmetic processing. The phase characteristics which differ depending on the wavelength of light at the overall measurement optical unit to be described in this embodiment include a phase characteristic which can be corrected in consideration of dispersion and an irregular phase characteristic which cannot be corrected even in consideration of dispersion. Arithmetic processing to be described in the embodiment corrects these two types of phase characteristics. Note that it is possible to execute a combination of the first and second embodiments. For example, within the already disclosed first embodiment, the first dichroic mirror 102 and the mirror 154-1 have phase characteristics corresponding to each other. Even if the incident angles of light on them differ from each other, the processing to be described below can reduce the influences of the incident angle difference and reliably acquire a tomographic image of the object 100, 202 to be examined with high accuracy.

The basic arrangement of an OCT apparatus according to the second embodiment is the same as the apparatus arrangement of the first embodiment described with reference to FIG. 1. The differences from the OCT apparatus arrangement of the first embodiment will be described below. In the second embodiment, the phase characteristics of optical elements, including a mirror 154-1 or a mirror 154-2 and a glass plate 155, on the reference optical path need not be the same as the phase characteristic of the at least one of dichroic mirrors 102, 103 as a component of an optical path branching unit. The mirror 154-1 or the mirror 154-2 may be a mirror having a metal film comprising aluminum, silver, gold, copper, or the like, or a mirror 154-1, 154-2 having the same phase characteristic as that of a first dichroic mirror 102. In addition, the glass plate 155 may be provided with a general antireflection film or may be a glass having the same phase characteristic as that of a second dichroic mirror 103.

Figure 6:
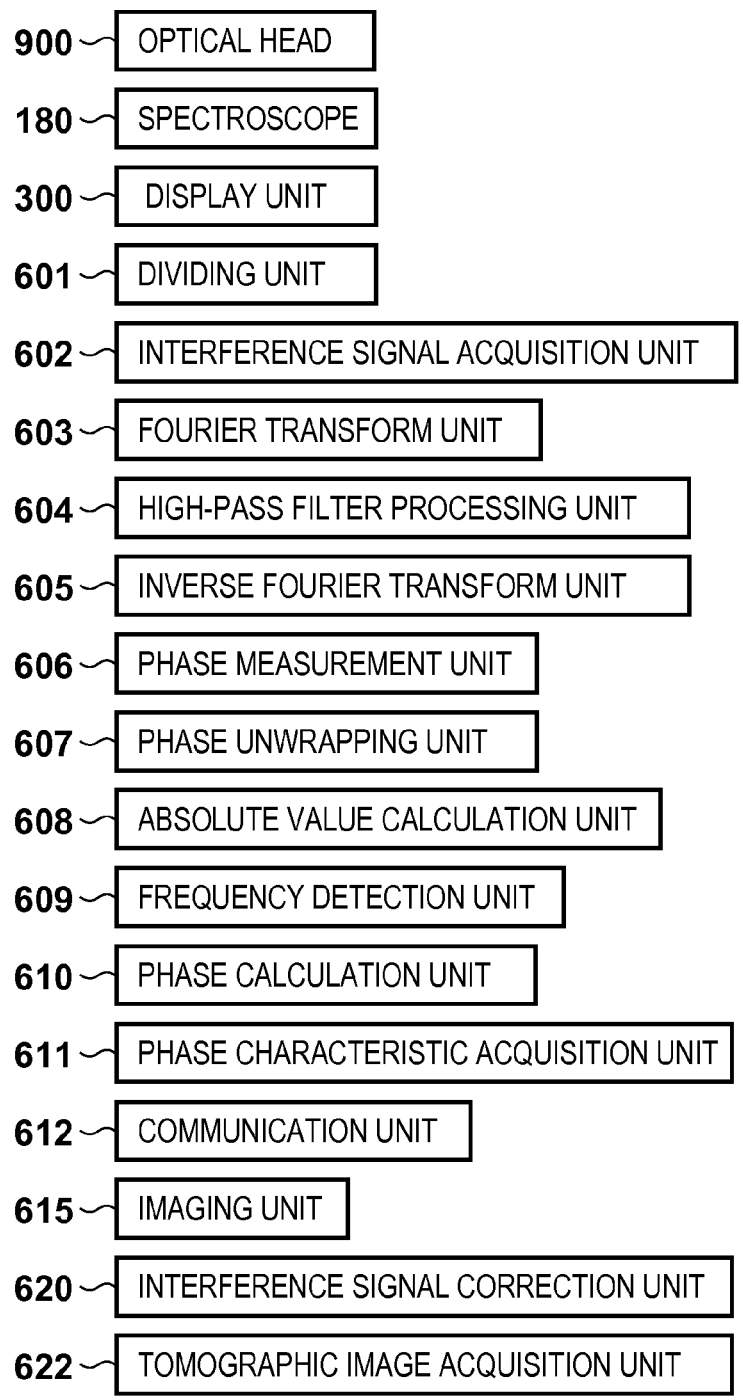
FIG. 6 is a view showing the functional arrangement of the optical coherence tomography apparatus according to the second embodiment.

FIG. 6 is a view for explaining the functional arrangement of the OCT apparatus according to the last embodiment. An optical head 900 in the last embodiment differs from that in the first embodiment in that the phase characteristics of the mirror 154-1 or the mirror 154-2 and the glass plate 155 are not specifically limited. Other arrangements of the optical head 900 and a spectroscope 180 are the same as those in the first embodiment. An imaging unit 615 acquires an image of a predetermined region of the object 100, 202 to be examined and based on return light from the object based on light from the light source 130. Note that the optical head 900 includes an optical path branching unit, including the first dichroic mirror 102 and the second dichroic mirror 103, which guides light to an object 100, 202 to be examined and guides return light from the object 100, 202 to an optical path in accordance with the wavelength.

A dividing unit 601 divides light from a measurement light source 130, which differs in wavelength from a light source 130 for imaging the anterior ocular segment, as a first region, or the fundus 202, as a second region, into reference light and measurement light.

An interference signal acquisition unit 602 acquires the spectrum of interference light received by a line sensor 184, and converts the intensity distribution of the spectrum of the interference light relative to the wavelength into an intensity distribution relative to the wave number. In this case, the line sensor 184 functions as a light receiving unit which receives the interference light between return light from the object 100, 202 to be examined based on measurement light and reference light. The interference signal acquisition unit 602 then obtains the difference between a measurement result on the intensity of the reference light and a measurement result on the intensity of the measurement light from the conversion result on the intensity distribution relative to the wave number. The interference signal acquisition unit 602 acquires the interference signal of the interference light between the return light from the object based on the measurement light guided via the optical path branching unit and the reference light by using this difference computation result.

A Fourier transform unit 603 performs Fourier transform for the interference signal acquired by the interference signal acquisition unit 602. A high-pass filter processing unit 604 performs high-pass filter processing for the signal having undergone the Fourier transform by the Fourier transform unit 603. Performing the high-pass filter processing will acquire only a positive-component signal of the positive and negative Fourier transform signals obtained by the Fourier transform by the Fourier transform unit 603. An inverse Fourier transform unit 605 performs inverse Fourier transform for the signal having undergone the high-pass filter processing by the high-pass filter processing unit 604.

A phase measurement unit 606 measures the phase of the interference signal by acquiring the deflection angle component of the interference signal acquired by the interference signal acquisition unit 602. A phase unwrapping unit 607 performs phase unwrapping processing for the phase measured by the phase measurement unit 606 to convert the discontinuous phase into a continuous phase.

An absolute value calculation unit 608 converts the positive-component signal obtained by the high-pass filter processing by the high-pass filter processing unit 604 into an absolute value. A frequency detection unit 609 detects the frequency of the interference signal represented by formula (ii) by detecting the peak position of the absolute value signal obtained by the absolute value calculation unit 608. A phase calculation unit 610 calculates the phase of the interference signal from the frequency of the interference signal detected by the frequency detection unit 609.

A phase characteristic acquisition unit 611 acquires information representing the phase characteristic of the interference light from the interference signal by subtracting the phase calculated by the phase calculation unit 610 from the phase of the real signal obtained by the phase unwrapping unit 607.

An interference signal correction unit 620 converts the interference signal acquired by the interference signal acquisition unit 602 into a complex-number form, and also converts information representing the phase characteristic acquired by the phase characteristic acquisition unit 611 into a complex-number form. The interference signal correction unit 620 then performs the arithmetic processing of multiplying the two complex-number forms. Based on the computation result obtained by the interference signal correction unit 620, the interference signal correction unit 620 separates the interference signal represented by formula (ii) into information of the object 100,202, which includes information representing the phase characteristic of the interference light and information of the object 100, 202 without including information representing the phase characteristic of the interference light.

Upon separating the information of the object 100, 202, which includes information representing the phase characteristic of the interference light and the information of the object which includes no information representing the phase characteristic of the interference light, the interference signal correction unit 620 converts the computation result on the complex-number forms into a real-number form. The computation processing performed by the interference signal correction unit 620 will separate the interference signal into information of the object 100,202 which includes information representing the phase characteristic of the interference light and the information of the object 100,202 which includes no information representing the phase characteristic of the interference light. The interference signal correction unit 620 then outputs, as a corrected interference signal, information of the object 100,202 of the separated information, which includes no information representing the phase characteristic of the interference light to a tomographic image acquisition unit 622.

The tomographic image acquisition unit 622 acquires a tomographic image of the object 100, 202 by using the information of the object including no information representing the phase characteristic of interference light separated from the interference signal based on the numerical processing result obtained by the interference signal correction unit 620.

The display unit 300 displays the two-dimensional anterior eye image and fundus image acquired by an imaging unit 615 and the tomographic image acquired by the tomographic image acquisition unit 622 side by side (FIG. 3).

Method of Capturing Tomographic Image

A method of capturing a tomographic image by using an image capturing apparatus will be described next. Similar the first embodiment, the image capturing apparatus can acquire a tomographic image of a desired region of an object 100, 202, for example the fundus of the eye, to be examined by controlling an X scanner 122-1 and a Y scanner 122-2. For example, as shown in FIG. 2, the apparatus irradiates the eye 100 with measurement light 201 and scans the fundus 202 in the x direction to acquire information corresponding to a predetermined imaging count from the imaging range of the fundus 202 in the x direction by using the line sensor 184.

Figure 4:
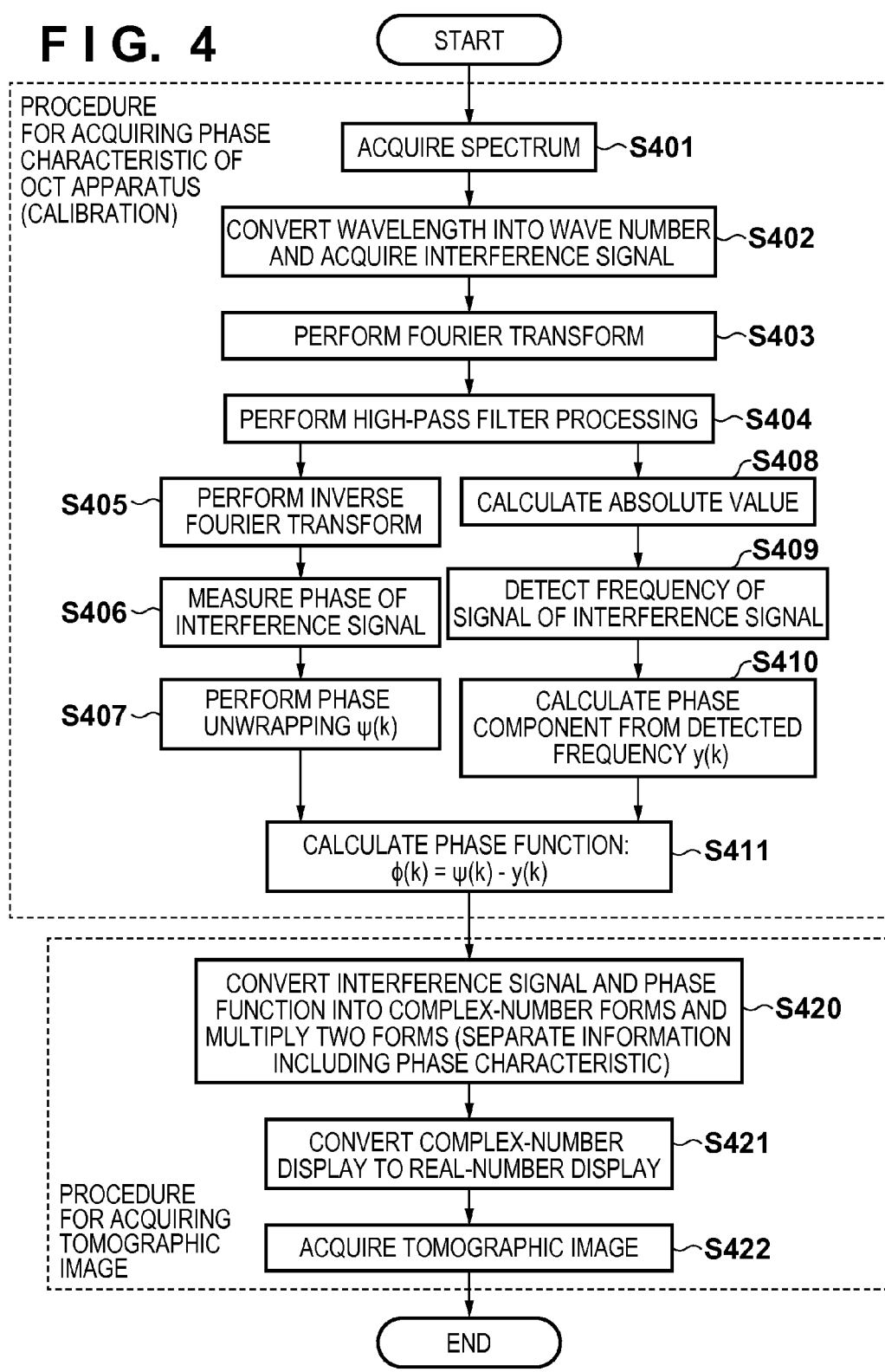
FIG. 4 is a flowchart for explaining a processing procedure by an optical coherence tomography apparatus according to the second embodiment.

FIG. 4 is a flowchart for explaining a processing procedure for performing calibration to acquire the phase characteristics of the overall measurement optical unit of the image capturing apparatus according to this embodiment and acquiring a tomographic image by correcting an interference signal based on the calibration result.

Calibration of Phase Characteristics of Image Capturing Apparatus

A calibration procedure for acquiring the phase characteristics of the overall measurement optical unit of the OCT apparatus will be described first. In step S401, the examiner places, as objects 100, 202 to be examined, a glass having the same dispersion amount as that of the eye 100, instead of the eye 100, and a mirror as a reflector at a position ($z_a$) corresponding to the fundus 202 position of the eye 100. The return light reflected by this mirror is guided by the optical path branching unit, including the first dichroic mirror 102 and the second dichroic mirror 103, to be returned to a fiber end 126. The interference signal acquisition unit 602 generates interference light by combining the return light and the reference light returned from the reference optical path using an optical coupler 125. The line sensor 184 of the spectroscope 180 receives the generated interference light via an optical fiber 125-4. The line sensor 184 functions as a light-receiving unit which receives the interference light between the return light from the object based on the measurement light and the reference light. The interference signal acquisition unit 602 acquires the spectrum of the interference light received by the line sensor 184.

In step S402, the interference signal acquisition unit 602 converts the intensity distribution of the spectrum of the interference light relative to the wavelength into an intensity distribution relative to the wave number. The relationship between wavelength and wave number is represented by $k=2\pi/\lambda$ (where k is the wave number and $\lambda$ is the wavelength). The intensity distribution relative to the wave number is defined by $$I = I_{ref} + I_{obj} + 2\sqrt{I_{ref}I_{obj}} \cos(kz_a + \phi(k)) \quad \text{(i)}$$

In this equation, $I_{ref}$ and $I_{obj}$ are respectively a signal representing the intensity of the reference light and a signal representing the intensity of the measurement light, $z_a$ is the coordinates of the mirror placed in the Z direction in FIG. 1, and $\phi(k)$ is information representing the phase characteristics of the overall measurement optical unit 114, 142, 184. Consider, for example, an optical path branching unit, such as the dichroic mirror 102, 103, as an optical element of the measurement optical unit. In this case, $\phi(k)$ is a phase function representing the phase characteristics of the optical path branching unit and is to be obtained. The apparatus also measures $I_{ref}$ and $I_{obj}$ upon shutting off one of the reference optical path and the measurement optical path by using a light-shielding unit such as a shutter (not shown) provided for each optical path. The interference signal acquisition unit 602 acquires the interference signal represented by formula (ii) by calculating the difference between the measurement results ($I_{ref}$ and $I_{obj}$) obtained from the conversion result on the intensity distribution relative to the wave number represented by equation (i).

$$2\sqrt{I_{ref}I_{obj}} \cos(kz_a + \phi(k)) \quad \text{(ii)}$$

In general, only a single frequency corresponding to the mirror position is observed. If the phase characteristics of the dichroic mirror 102, 103 indicate a phase characteristic, which can be corrected in consideration of dispersion, and an irregular phase characteristic, which cannot be corrected even in consideration of dispersion, the frequencies of a plurality of interference signals to which $\phi(k)$ corresponding to the wave number (k) is added are observed.

In step S403, the Fourier transform unit 603 performs Fourier transform for the interference signal acquired in step S402.

In step S404, the high-pass filter processing unit 604 acquires only the positive-component signal of the positive and negative Fourier transform signals obtained in step S403 by performing high-pass filter processing for the signal having undergone the Fourier transform.

In step S405, the inverse Fourier transform unit 605 performs inverse Fourier transform for the positive-component signal acquired by the high-pass filter processing in step S404.

In step S406, the phase measurement unit 606 measures the phase of the interference signal. Acquiring the positive-component signal by the high-pass filter processing in step S404 can express the signal in polar representation. The phase measurement unit 606 can measure the phase of the interference signal by acquiring a deflection angle component from the interference signal expressed in polar representation.

In step S407, the phase unwrapping unit 607 performs phase unwrapping processing for the phase measured in step S406 to convert discontinuous phases between −360° and +360° into a continuous phase. The phase obtained in this case is represented by $\psi(k)$ (where k is a wave number).

In step S408, the absolute value calculation unit 608 converts the positive-component signal obtained by the high-pass filter processing in step S404 into an absolute value.

In step S409, the frequency detection unit 609 detects the frequency of the interference signal represented by formula (ii) by detecting the peak position of the positive-component signal of the absolute value obtained by the processing in step S408.

In step S410, the phase calculation unit 610 calculates the phase represented by equation (iii) from the frequency of the interference signal detected in step S409.

$$y(k) = 2\pi f \frac{k}{N} \quad \text{(iii)}$$

In this equation, y(k) is a phase, k is a wave number, and N is the number of pixels of the line sensor 184. In this case, the phase calculation unit 610 calculates the phase component of the interference signal by the arithmetic processing represented by equation (iii) using a frequency f obtained in step S409.

In step S411, the phase characteristic acquisition unit 611 obtains the difference between the phase ($\psi(k)$) of the real signal obtained in step S407 and the phase (y(k)) calculated in step S410 according to equation (iv). The phase characteristic acquisition unit 611 acquires phase function $\phi(k)$ representing the phase characteristic of the interference light from the interference signal by the differential processing represented by equation (iv):

$$\phi(k) = \psi(k) - y(k) \quad \text{(iv)}$$

If phase characteristics include a phase characteristic, which can be corrected in consideration of dispersion, and an irregular phase characteristic, which cannot be corrected even in consideration of dispersion, the phase function $\phi(k)$ representing the phase characteristic of the interference light represented by equation (iv) is added as defined within formula (ii). In this case, the apparatus performs the processing in step S420 and the subsequent steps to perform the correction processing of removing the influence of the phase characteristic from the interference signal by using the phase function $\phi(k)$ representing the phase characteristic acquired by calibration.

Note that this embodiment has exemplified the case in which the phase characteristics of the overall measurement optical unit in the OCT apparatus are acquired by arithmetic processing in the OCT apparatus. The scope of the present invention is not limited to this case. The embodiment may be configured to store, in advance outside the OCT apparatus, the measurement results obtained by measuring the phase characteristics of the overall measurement optical unit and acquire the measurement results on the phase characteristics of the overall measurement optical unit of the OCT apparatus from an external database or server. In this case, the OCT apparatus includes a communication unit 612 for acquiring data by communicating with the external database or server. The display unit 300 displays the data acquired via the communication unit 612. The examiner can check the data acquired via the communication unit 612.

The following description is a processing procedure for performing the correction processing of removing the influences of the phase characteristics of the overall measurement optical unit from the interference signal by numerical arithmetic processing and acquiring a tomographic image based on the corrected interference signal.

Acquisition of Tomographic Image

In step S420, the interference signal correction unit 620 separates the interference signal represented by formula (ii) into information (signal) of the object which includes information representing the phase characteristic of the interference light and information (signal) of the object which includes no information representing the phase characteristic of the interference light.

In this step, first of all, the interference signal correction unit 620 converts the interference signal (formula (ii)) extracted in step S402 into a complex-number form. Likewise, the interference signal correction unit 620 converts the phase (formula (iv)) acquired in step S411 into a complex-number form (for example, $e^{-i(\phi(k))}$). The interference signal correction unit 620 then performs the arithmetic processing of multiplying the interference signal converted into the complex-number form by the phase. This arithmetic processing result is represented by formula (v):

$$\sqrt{I_{ref}I_{obj}}(e^{i(kz+\phi(k))}+e^{-i(kz+\phi(k))})e^{-\phi(k)} \quad (v)$$

Expanding formula (v) and omitting $\sqrt{I_{ref}I_{obj}}$ will obtain formula (vi):

$$e^{ikz}+e^{-i(kz+2\phi(k))} \quad (vi)$$

The second term of formula (vi) is extracted as a signal including information representing the phase characteristic of the interference light and including phase function $\phi(k)$ representing the phase characteristics of the overall measurement optical unit. The first term of formula (vi) represents a signal including no information representing the phase characteristic of the interference light and being free from phase function $\phi(k)$ representing the phase characteristics of the overall measurement optical unit. This processing extracts only the information of the object 100, 202 from which the influences of the overall measurement optical unit, for example, the influences of the first dichroic mirror 102, of the second dichroic mirror 103, of the mirror 121, and of the optical fiber 125-2 within the OCT apparatus are excluded.

Figure 5:
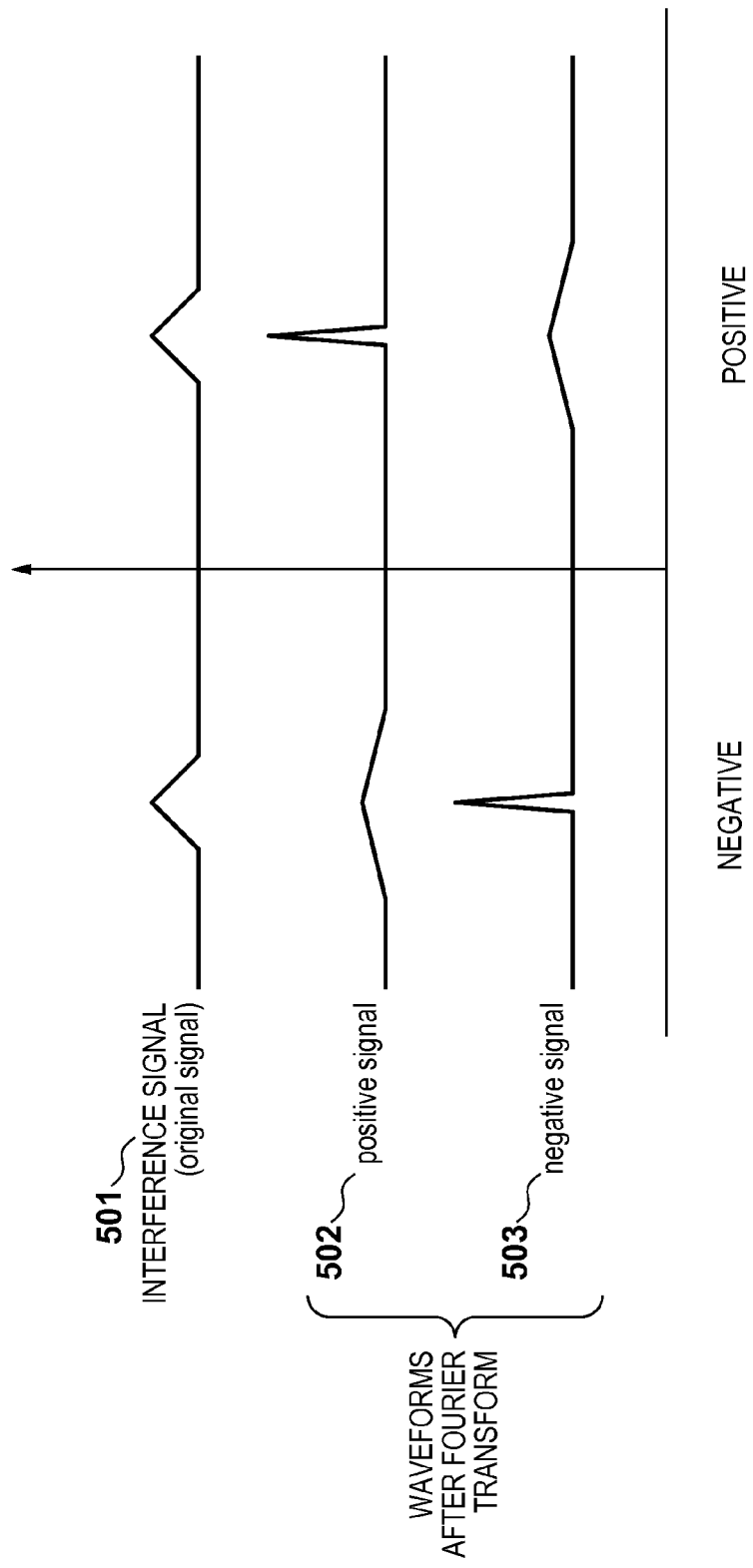
FIG. 5 is a view exemplifying an interfering signal and signal waveforms after the Fourier transform of the interfering signal.

FIG. 5 is a view exemplifying an interference signal 501 and the waveforms of signals obtained by performing Fourier transform for the interference signal. An interference signal 501 includes signals on the positive and negative sides, each having a waveform exhibiting a low peak, a moderate rise to the peak, and a broad interval between the leading and trailing portions of the peak. A positive signal 502 is obtained by Fourier transform for the signal represented by formula (vi), with a waveform exhibiting a steep rise to a high peak on the positive side. This is a signal corresponding to the first term ($e^{ikz}$) of formula (vi). The signal corresponding to the first term is a signal including no information representing the overall phase characteristics of the measurement optical unit including no information representing the phase characteristic of the interference light. This signal corresponds to only the information of the object 100, 202.

In contrast to this, the waveform of the positive signal 502 on the negative side exhibits a lower peak than that of the interference signal 501, a moderate rise to the peak, and a broader interval between the leading and trailing portions of the peak than that of the interference signal 501. This is a signal corresponding to the second term ($e^{-i(kz+2\phi(k))}$) of formula (vi). The signal corresponding to the second term is a signal including information representing the phase characteristics of the overall measurement optical unit including information representing the phase characteristic of the interference light.

The arithmetic processing in step S420 has exemplified the case in which the interference signal is multiplied by $e^{-i\phi(k)}$ as a complex-number form of the phase function. Multiplying the interference signal by $e^{+i\phi(k)}$ as a complex-number form of the phase function will obtain signal like a negative signal 503 in FIG. 5 with a waveform exhibiting a steep rise to the high peak on the negative side.

For this reason, in case a positive signal is used as an OCT signal, it is preferable to multiply the interference signal 501 by $e^{-i\phi(k)}$. Obviously, when a negative signal is used as an OCT signal, it is preferable to multiply the interference signal 501 by the exponential function $e^{+i\phi(k)}$. The processing in step S420 is performed for each A scan.

In step S421, the interference signal correction unit 620 converts formula (vi) computed in the complex-number form in step S420 into a real-number form. The interference signal correction unit 620 outputs, to the tomographic image acquisition unit 622 as a corrected interference signal, a signal based on the object which includes no information representing the phase characteristic of the overall measurement optical unit including no information representing the phase characteristic of interference light of the separated signal.

In step S422, the tomographic image acquisition unit 622 acquires a tomographic image of the object by using the signal which is separated from the interference signal in steps S420 and S421 and includes no information representing the phase characteristic of the interference light. The apparatus uses the same method of constructing a B scan image from A scan images as the first embodiment. The display unit 300 displays the acquired tomographic image in the same manner as in the first embodiment (FIG. 3). Using a signal including no information representing the phase characteristic of interference light makes it possible to acquire a tomographic image of the object 100, 202 to be examined with high accuracy even if the phase characteristics of the overall measurement optical unit include a phase characteristic which can be corrected in consideration of dispersion and an irregular phase characteristic which cannot be corrected even in consideration of dispersion.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190642, filed Aug. 30, 2012, which is hereby incorporated by reference herein in its entirety.

What is claimed is:

1. An image capturing apparatus comprising:
   a dividing unit configured to divide light from a measurement light source into reference light and measurement light;
   a light receiving unit configured to receive interference light between (a) return light from an object to be examined based on the measurement light and (b) the reference light;
   an interference signal acquisition unit configured to acquire an interference signal based on the interference light received by said light receiving unit;
   an interference signal correction unit configured to separate the interference signal into a signal including information representing a phase characteristic of the interference light and a signal including no information representing the phase characteristic of the interference light; and
   a tomographic image acquisition unit configured to acquire a tomographic image of the object by using the signal including no information representing the phase characteristic of the interference light,
   wherein said dividing unit comprises an optical coupler,
   wherein said light receiving unit comprises a line sensor, and
   wherein said interference signal acquisition unit, said interference signal correction unit, and said tomographic image acquisition unit are implemented using a processor.

2. The image capturing apparatus according to claim 1, wherein said interference signal correction unit separates the interference signal into the signal including information representing the phase characteristic of the interference light and the signal including no information representing the phase characteristic of the interference light based on calibration information.

3. The image capturing apparatus according to claim 2, further comprising:
   a phase characteristic acquisition unit that is implemented using the processor and that is configured to acquire information representing a phase characteristic of the image capturing apparatus as the calibration information.

4. The image capturing apparatus according to claim 3, wherein said phase characteristic acquisition unit acquires information representing a phase characteristic of an optical unit of the image capturing apparatus as the calibration information.

5. The image capturing apparatus according to claim 3, further comprising:
   a Fourier transform unit configured to perform Fourier transform for the a calibration interference signal based on interference light between (a) return light from an object for a calibration based on the measurement light and (b) the reference light:
   a filter processing unit configured to acquire a positive-component signal by performing high-pass filter processing for the Fourier-transformed signal;
   a phase measurement unit configured to measure a phase of the calibration interference signal by acquiring a deflection angle component from the signal having undergone the high-pass filter processing;
   a frequency detection unit configured to detect a frequency of the calibration interference signal by detecting a peak of the signal having undergone the high-pass filter processing; and
   a phase calculation unit configured to calculate a phase of the calibration interference signal from the frequency,
   wherein said phase characteristic acquisition unit acquires the information representing the phase characteristic of the image capturing apparatus from a difference between the measured phase of the calibration interference signal and the calculated phase of the calibration interference signal, and wherein said Fourier transform unit, said filter processing unit, said phase measurement unit, said frequency detection unit, and said phase calculation unit are implemented using the processor.

6. The image capturing apparatus according to claim 5, wherein the interference signal correction unit separates the interference signal into the signal including information representing the phase characteristic of the interference light and the signal including no information representing the phase characteristic of the interference light by multiplying the interference signal and the information representing the phase characteristic of the image capturing apparatus together.

7. The image capturing apparatus according to claim 5, wherein the object for the calibration includes (1) a reflector and (2) a glass.

8. The image capturing apparatus according to claim 1, further comprising an imaging unit configured to acquire an image of a predetermined region of the object based on return light from the object based on light from a light source different from the measurement light source,
   wherein said imaging unit comprises (1) a first imaging unit configured to acquire an image of a first region of the object based on return light from the object based on light having a first wavelength different from a wavelength of light from the measurement light source, and (2) a second imaging unit configured to acquire an image of a second region of the object different from the first region based on return light from the object based on light having a second wavelength different from a wavelength of light from the measurement light source and the first wavelength,
   wherein said first imaging unit comprises a CCD, and
   wherein said second imaging unit comprises a CCD.

9. The image capturing apparatus according to claim 8, further comprising a display unit configured to display an image acquired by said imaging unit and the tomographic image acquired by said tomographic image acquisition unit side by side.

10. The image capturing apparatus according to claim 1, wherein the object to be examined is a fundus of an eye.

11. An imaging method for an image capturing apparatus, the method comprising:
    a dividing step of dividing light from a measurement light source into reference light and measurement light;
    a light receiving step of receiving interference light between (a) return light from an object to be examined based on the measurement light and (b) the reference light;
    an interference signal acquisition step of acquiring an interference signal based on the interference light received in the light receiving step;
    an interference signal correction step of separating the interference signal into a signal including information representing a phase characteristic of the interference light and a signal including no information representing the phase characteristic of the interference light; and a tomographic image acquisition step of acquiring a tomographic image of the object by using the signal including no information representing the phase characteristic of the interference light.

12. A non-transitory computer-readable storage medium storing a program for causing a computer to execute an imaging method for an image capturing apparatus, the method comprising:

a dividing step of dividing light from a measurement light source into reference light and measurement light;

a light receiving step of receiving interference light between (a) return light from an object to be examined based on the measurement light and (b) the reference light;

an interference signal acquisition step of acquiring an interference signal based on the interference light received in the light receiving step;

an interference signal correction step of separating the interference signal into a signal including information representing a phase characteristic of the interference light and a signal including no information representing the phase characteristic of the interference light; and a tomographic image acquisition step of acquiring a tomographic image of the object by using the signal including no information representing the phase characteristic of the interference light.

\* \* \* \* \*